US005514530A

United States Patent [19]
Merkel et al.

[11] Patent Number: 5,514,530
[45] Date of Patent: * May 7, 1996

[54] PHOTOGRAPHIC ELEMENTS COMPRISING 2-PHENYLCARBAMOYL-1-NAPHTHOL IMAGE-MODIFYING COUPLERS YIELDING DYES RESISTANT TO CRYSTALLIZATION AND REDUCTION

[75] Inventors: Paul B. Merkel; Jerrold N. Poslusny, both of Rochester; Melvin M. Kestner, Hilton; Ronald E. Leone, Rochester; David A. Steele, Webster, all of N.Y.

[73] Assignee: Eastman Kodak Company, Rochester, N.Y.

[*] Notice: The portion of the term of this patent subsequent to Jul. 28, 2013, has been disclaimed.

[21] Appl. No.: 98,692

[22] Filed: Jul. 28, 1993

[51] Int. Cl.$^6$ .............................. G03C 7/305; G03C 7/34
[52] U.S. Cl. .................... 430/544; 430/553; 430/957
[58] Field of Search ...................... 430/955, 956, 430/957, 958, 543, 544, 553, 561–563, 549

[56] References Cited

U.S. PATENT DOCUMENTS

| | | | |
|---|---|---|---|
| 3,459,552 | 1/1966 | Yoshida et al. | 96/100 |
| 3,488,193 | 1/1970 | Eynde et al. | 96/55 |
| 4,725,530 | 2/1988 | Kobayashi et al. | 430/505 |
| 4,840,884 | 6/1989 | Mooberry et al. | 430/557 |
| 4,857,442 | 8/1989 | Fujita et al. | 430/553 |
| 4,883,746 | 11/1989 | Shimada et al. | 430/504 |
| 4,912,024 | 3/1990 | Michno et al. | 430/558 |
| 4,957,853 | 9/1990 | Kobayashi et al. | 430/384 |
| 4,962,018 | 10/1990 | Szajewski et al. | 430/558 |
| 5,085,979 | 2/1992 | Yamagami et al. | 430/957 |
| 5,114,835 | 5/1992 | Sakanoue | 430/393 |
| 5,250,405 | 10/1993 | Merkel et al. | 430/544 |

FOREIGN PATENT DOCUMENTS

| | | | |
|---|---|---|---|
| 676750 | 12/1963 | Canada | 96/102 |
| 0193389 | 10/1990 | European Pat. Off. | G03C 7/32 |
| 2454329 | 5/1975 | Germany. | |
| 62-247363 | 10/1987 | Japan | G03C 7/34 |
| 5107706 | 4/1993 | Japan | 430/955 |
| 1111342 | 4/1968 | United Kingdom | G03C 7/34 |

*Primary Examiner*—Lee C. Wright
*Attorney, Agent, or Firm*—Peter C. Cody

[57] ABSTRACT

Photographic elements comprising certain 2-phenylcarbamoyl-1-naphthol image-modifying couplers exhibit proper hue, a resistance to dye crystallization, and a resistance to leuco cyan dye formation. Such couplers can be utilized for their image-modifying effect and can contribute substantially to the overall dye density of an image.

19 Claims, No Drawings

PHOTOGRAPHIC ELEMENTS COMPRISING 2-PHENYLCARBAMOYL-1-NAPHTHOL IMAGE-MODIFYING COUPLERS YIELDING DYES RESISTANT TO CRYSTALLIZATION AND REDUCTION

FIELD OF THE INVENTION

This invention relates to photographic elements and to novel two-equivalent 2-phenylcarbamoyl-1-naphthol image-modifying couplers.

BACKGROUND

Modern photographic materials, particularly color negative films, contain a variety of so-called image modifying couplers including development inhibitor releasing (DIR) couplers, switched or timed inhibitor releasing (DIAR) couplers, bleach accelerator releasing couplers (BARCs) and colored masking couplers. DIR couplers, such as those described in U.S. Pat. No. 3,227,554, and DIAR couplers, such as those described in U.S. Pat. No. 4,248,962, perform such useful functions as gamma or curve shape control, sharpness enhancement, granularity reduction and color correction. BARCs, such as those described in European Patent Application 193,389, facilitate the oxidation of developed silver in bleach solutions. They may also enhance silver developability, thereby affecting gamma. Masking couplers, such as those described in J. Opt. Soc. Am, 40, 171 (1950) and in U.S. Pat. No. 2,428,054, are used to correct for the unwanted absorptions of various imaging dyes.

Modern color negative films often contain both image couplers, which contribute solely to the production of dye, and image-modifying couplers, such as those described above. The image-modifying couplers, in addition to having an image modifier component (e.g. bleach accelerator or development inhibitor), also comprise an image dye parent. In films which comprise both image couplers and image-modifying couplers, much of the ultimate color density exhibited by the film is often derived from the parent of the image-modifying coupler.

Many films today contain large amounts of such image-modifying couplers in the red-sensitive, cyan-dye-containing layers. These image-modifying couplers typically have cyan image dye parents which generate cyan dye upon reaction of the image-modifying couplers with oxidized developer. Because such cyan dye substantially contributes to the total red density in these films, it is important that the dyes generated from the image-modifying couplers have suitable properties. Desirable properties include good hue, good stability, resistance to reduction in seasoned bleaches or in bleaches of low oxidizing strength, and resistance to hue changes on storage at low temperatures.

Resistance to reduction in seasoned bleaches is particularly important because certain cyan dyes are prone to being reduced by ferrous ion complexes (such as ferrous EDTA) and other reducing agents, which are found in seasoned bleach solutions. When reduced, these cyan dyes form leuco cyan dyes (LCD formation). Leuco cyan dyes are colorless and, thus, films containing couplers which are easily converted into leuco cyan dyes exhibit substantial loss (and variability) in color density during processing.

Resistance to hue changes upon storage at low temperatures is also of particular importance. Certain cyan dyes tend to crystallize at low temperatures. This naturally affects the hue of such dyes, and it ultimately leads to inaccurate color and tone reproduction in films which have been stored at low temperatures, and which contain these dyes.

From the above, it can be seen that a need exists for image-modifying couplers which are capable of being used in conjunction with image couplers, and which can contribute substantially to the overall color density of an image. Furthermore, a need exists that the dyes generated from such image-modifying couplers be resistant to reduction in seasoned bleaches and be resistant to crystallization at low temperatures.

Certain of the above needs have been provided by known couplers having a 2-phenylcarbamoyl-1-naphthol structure. However, such couplers do not enable all of the above needs to be met. Image couplers, for instance, are known which yield dyes that are resistant to reduction in seasoned bleaches (U.S. Pat. Nos. 3,488,193 and 4,957,853). However, these couplers often crystallize at low temperatures. Furthermore, U.S. Pat. No. 4,957,853 discloses that these couplers should not be combined with photographically useful groups to form image-modifying couplers. Such a combination would impair the photographic properties of a photographic element containing the image-modifying couplers.

Bleach accelerator releasing couplers, development inhibitor releasing couplers (both timed and untimed, switched and unswitched), and masking couplers, having a 2-phenylcarbamoyl-1-naphthol structure, are also known (EP 0193389, Japanese Kokai JP62-247363, U.S. Pat. No. 4,725,530, DE 2,454,329, British Patent 1,111,342, Japanese Kokai JP62-087959, U.S. Pat. No. 3,459,552, and U.S. Pat. No. 4,883,746). Several of these image-modifying couplers, however, provide dyes which crystallize at low temperatures. Several others provide dyes which are prone to reduction in seasoned bleach, or which exhibit improper hue; and still others have insufficient or improper image-modifying effect.

As noted, a need exists to provide for image-modifying couplers which are capable of being used in conjunction with image couplers, and which can contribute substantially to the overall color density of an image. Furthermore, a need exists that such image-modifying couplers be resistant to reduction in seasoned bleaches and be resistant to crystallization at low temperatures.

SUMMARY OF THE INVENTION

In this regard, the present invention solves these problems by providing a photographic element comprising a support bearing (a) at least one silver halide emulsion and (b) at least one cyan dye-forming 2-phenylcarbamoyl-1-naphthol image-modifying coupler having the structure

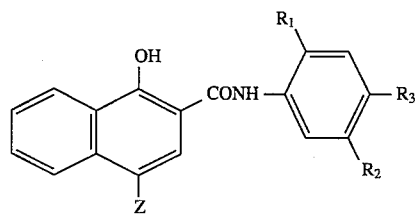

wherein:

$R_1$ is selected from an alkoxy group, a phenoxy group and halogen;

$R_2$ is selected from the group consisting of an alkyl group, a phenyl group, an alkoxy group, an alkoxycarbonyl group, and a halogen;

$R_3$ is selected from hydrogen, and an alkyl group;

$R_1$, $R_2$, and $R_3$ together contain at least 3 carbon atoms; and

Z is a development inhibitor releasing group having the structure:

wherein:

IN is a development inhibitor moiety;

TIME is a timing group or switch capable of releasing the inhibitor moiety by means of intramolecular nucleophilic displacement reaction or electron transfer reaction down a conjugated chain; and w is 1, 2, or 3.

In one embodiment of the invention, the photographic element comprises a coupler as defined above, but wherein $R_2$ is selected from the group consisting of an unsubstituted or substituted alkyl group, an unsubstituted or substituted phenyl group, an unbranched unsubstituted alkoxy group, a halogen, and an alkoxycarbonyl group; with the proviso that when $R_2$ is an alkoxycarbonyl group or halogen, $R_1$ is an alkoxy or a phenoxy group.

In another embodiment, the photographic element comprises a coupler as defined above, but wherein $R_1$ is selected from an unsubstituted unbranched alkoxy group, and a substituted alkoxy group having less than six carbon atoms.

In yet another embodiment, the photographic element comprises a coupler as defined above, but wherein $R_2$ is selected from the group consisting of an alkyl group, a phenyl group, an alkoxy group, which is preferably unbranched and unsubstituted, and a halogen; with the proviso that when $R_2$ is a halogen, $R_1$ is an alkoxy or a phenoxy group.

The particular selection of substituents on the phenyl group of the 2-phenylcarbamoyl-1-naphthol image-modifying coupler, as well as the particular placement of the substitutents at ortho and meta positions, has been found to impart surprising characteristics to the photographic elements of the invention. Specifically, photographic elements comprising couplers in accordance with the invention exhibit proper hue, a resistance to dye crystallization, and a resistance to leuco cyan dye formation.

DETAILED DESCRIPTION OF THE INVENTION

The present invention concerns image-modifying couplers having the structure defined below, and photographic elements containing such couplers. Specifically, the invention concerns photographic elements comprising a cyan dye-forming 2-phenylcarbamoyl-1-naphthol image-modifying coupler having the structure I

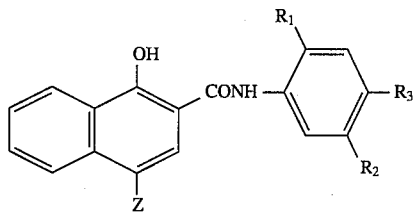

wherein:

$R_1$ is selected from an alkoxy group (preferably unsubstituted and unbranched), a phenoxy group and halogen;

$R_2$ is selected from the group consisting of an alkyl group, a phenyl group, an alkoxy group (preferably unbranched and unsubstituted), an alkoxycarbonyl group, and a halogen;

$R_3$ is selected from hydrogen, and an alkyl group;

$R_1$, $R_2$, and $R_3$ together contain at least 3 carbon atoms, although it is preferred that $R_1$, $R_2$, and $R_3$ together contain at least 9 carbon atoms, and most preferred that $R_1$, $R_2$, and $R_3$ together contain from 12 to 30 carbon atoms; and Z is a development inhibitor releasing group having the structure:

wherein:

IN is a development inhibitor moiety;

TIME is a timing group or switch capable of releasing the inhibitor moiety by means of intramolecular nucleophilic displacement reaction or electron transfer reaction down a conjugated chain; and w is 1, 2, or 3.

As used herein, the term electron transfer reaction down a conjugated chain is understood to refer to transfer of an electron along a chain of atoms in which alternate single and double bonds occur. A conjugated chain is understood to have the same meaning as commonly used in organic chemistry.

As used herein, the term intramolecular nucleophilic displacement reaction refers to a reaction in which a nucleophilic center of a compound reacts directly or indirectly through an intervening molecule, at another site on the compound, which is an electrophilic center, to effect displacement of a group or atom attached to the electrophilic center. Such compounds have a nucleophilic group and electrophilic group spatially related by configuration of the molecule to promote reactive proximity. Preferably, the nucleophilic group and electrophilic group are located in the compound so that a cyclic organic ring, or a transient cyclic organic ring, can easily be formed by an intramolecular reaction involving the nucleophilic center and the electrophilic center.

Preferably Z is selected from the structures:

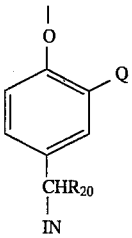

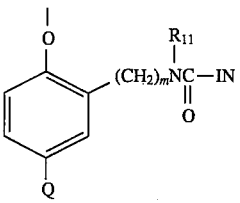

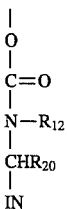

wherein:

m is 0 or 1;

Q is an electron withdrawing group, examples of which include nitro, cyano, halo, carbamoyl, alkylsulfonyl, sulfamoyl and sulfonamido groups;

$R_{11}$ is selected from an alkyl group containing from 1 to 8 carbon atoms, and a phenyl group;

$R_{12}$ is an alkyl group, preferably containing from 1 to 8 carbon atoms;

$R_{20}$ is a hydrogen or an alkyl group; preferably containing from 1 to 8 carbon atoms when $R_{20}$ is an alkyl group; and IN is a development inhibitor moiety.

Z may also be a development inhibitor releasing group containing an inhibitor moiety and timing group, wherein the timing group is a heterocyclic timing group. Examples of heterocyclic timing groups are disclosed in U.S. Pat. Nos. 4,409,323 and 4,421,845, and in JP-A-57-188035, JP-A-58-98728, JP-A-58-209736, JP-A-58-209737 and JP-A-58-209738.

As used herein, substituents described without reference to branching or substitutions are to be construed as optionally containing branching and/or substitutions.

Also as used herein, alkoxycarbonyl is to be defined as a group having the structure $COOR_5$, wherein $R_5$ is an alkyl group.

Preferably, the image-modifying coupler of the present invention comprises an inhibitor moiety, IN, selected from the structures:

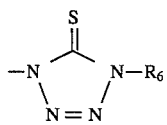

II

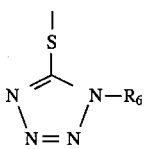

III

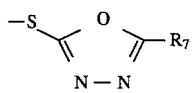

IV

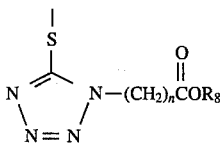

V

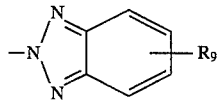

VI

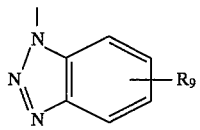

VII wherein:

$R_6$ is selected from the group consisting of an alkyl group containing from 1 to 8 carbon atoms, a benzyl group, and a phenyl group; optionally substituted, preferably with at least an alkoxy group;

$R_7$ is $R_{13}$ or $—SR_{13}$ wherein $R_{13}$ is selected from the group consisting of an alkyl group containing from 1 to 8 carbon atoms, a benzyl group, and a phenyl group; optionally substituted, preferably with at least one alkoxy group;

$R_8$ is an alkyl group containing 1 to 5 carbon atoms;

$R_9$ is selected from the group consisting of hydrogen, halogen, alkoxy, phenyl, $—COOR_{10}$ and $NHCOOR_{10}$, wherein $R_{10}$ is an alkyl group, an alkylthio group, or a phenyl group; and n is from 1 to 3.

More preferably, the image-modifying coupler of the present invention comprises an inhibitor moiety having structure III (above) with $R_6$ as a phenyl or a p-methoxybenzyl group; or having structure V with n equal to one and $R_8$ as propyl. In such instances, it is preferred that the inhibitor moiety be associated with the image-modifying coupler via a development inhibitor releasing group(Z) having the structure:

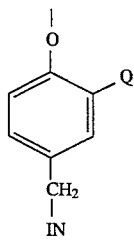

wherein Q is a nitro group (or other electron-withdrawing group), and IN has the structure defined above.

Other development inhibitor releasing groups(Z) capable of being utilized in accordance with the invention are defined by structures below:

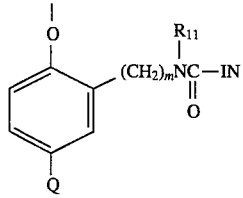

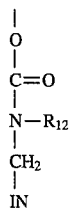

wherein:

Q is an electron-withdrawing group, such as a nitro, cyano, carbamoyl, alkylsulfonyl, sulfamoyl or sulfonamido group; m is 0 or 1; $R_{11}$ is selected from the group consisting of straight or branched chain alkyl groups containing from 1 to 8 carbon atoms, and unsubstituted or substituted phenyl groups; $R_{12}$ is an alkyl group; and IN is a development inhibitor moiety exemplified above in formulas II–VII.

In the more preferred embodiments of the invention, the couplers are defined as above (structure I) except that $R_2$ is selected from the group consisting of an unsubstituted or substituted alkyl group, an unsubstituted or substituted phenyl group, an unbranched unsubstituted alkoxy group, a halogen, and an alkoxycarbonyl group; with the proviso that when $R_2$ is an alkoxycarbonyl group or halogen, $R_1$ is an alkoxy or a phenoxy group. Also preferred is where $R_2$ is selected from the group consisting of an alkyl group, a phenyl group, an alkoxy group, and a halogen; with the proviso that when $R_2$ is a halogen, $R_1$ is selected from an alkoxy or a phenoxy group. In the above instances, when either $R_1$ or $R_2$ is an alkoxy group, it is preferred that the group be unsubstituted and unbranched.

The couplers may also be defined as above, but where $R_1$ is selected from an unsubstituted unbranched alkoxy group, and a substituted alkoxy group having less than six carbon atoms.

Other preferred embodiments comprise couplers wherein $R_1$ is an unsubstituted, unbranched alkoxy group, $R_2$ is an unsubstituted alkyl group, $R_3$ is hydrogen, and $R_1$, $R_2$, and $R_3$ together contain at least 9 carbon atoms. Within this embodiment, it is even more preferred that $R_1$ be an n-dodecyloxy group and $R_2$ be a methyl group; or that $R_1$ be selected from an n-dodecyloxy group and an n-decyloxy group, and $R_2$ be a secondary butyl group.

In yet another preferred embodiment, the couplers are as defined above in structure I except that $R_1$ is an unsubstituted, unbranched alkoxy group, $R_2$ is an alkoxycarbonyl group, $R_3$ is hydrogen, and $R_1$, $R_2$, and $R_3$ together contain at least 9 carbon atoms. Within this embodiment, it is preferred that $R_1$ be an n-octyloxy group and $R_2$ be a 2-ethylhexoxycarbonyl group.

Other preferred embodiments of the invention include couplers as defined above, but wherein when $R_1$ is an alkoxy group and $R_2$ is an alkoxycarbonyl group, IN is an inhibitor moiety other than a 1-phenyl-1H-tetrazole- 5-thio group or a 2-carboxy-phenyl-thio group.

Examples of 2-phenylcarbamoyl-1-naphthol DIAR couplers according to this invention include, but are not limited to, the following:

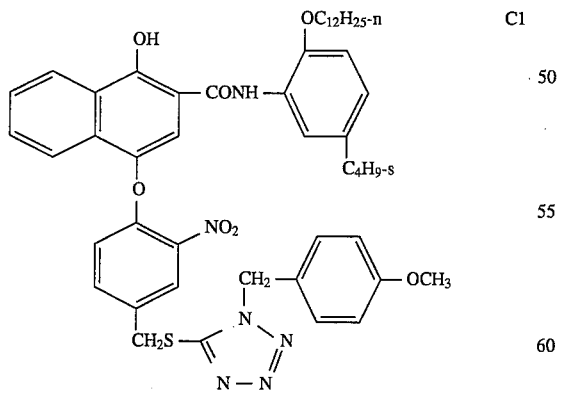

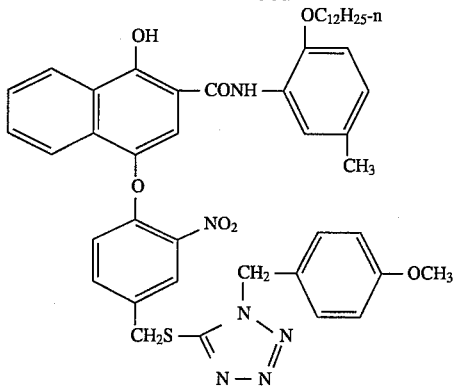

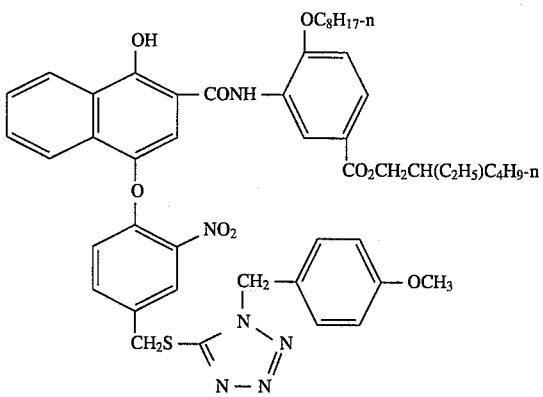

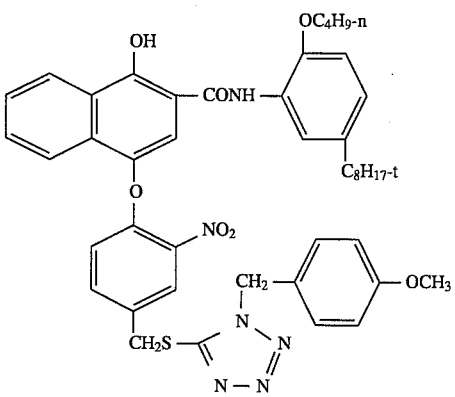

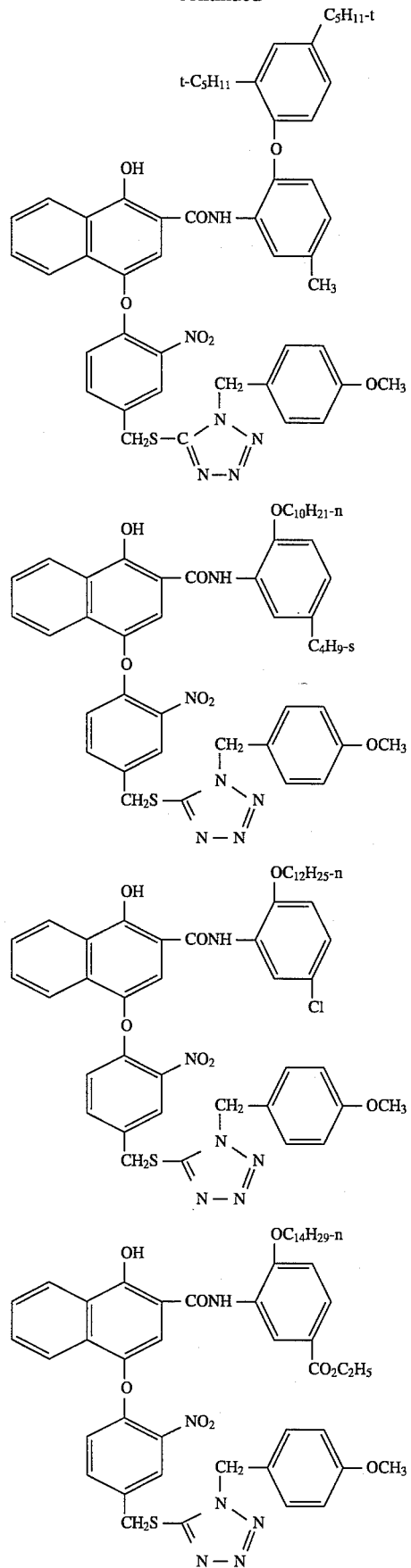
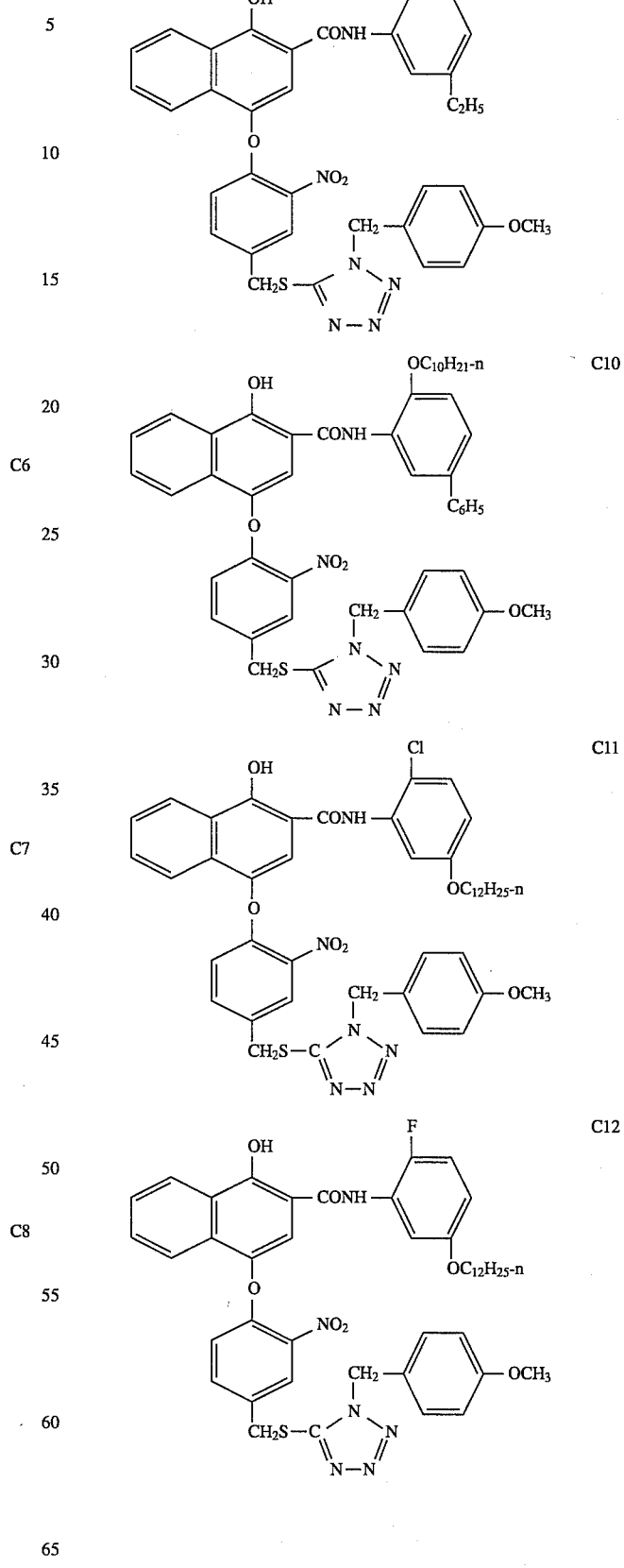

-continued
C13
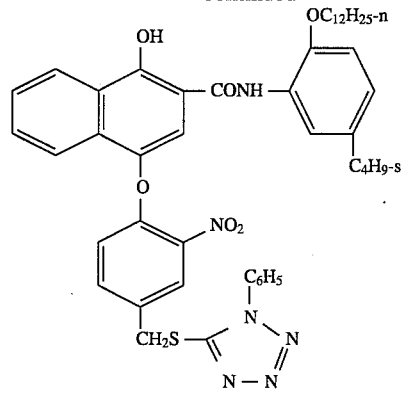
C14
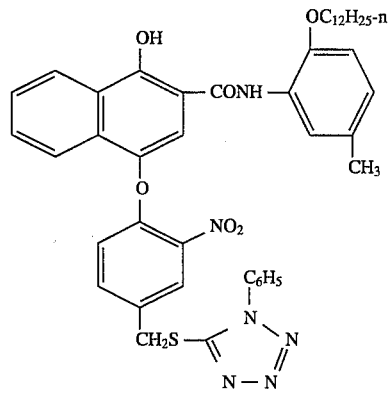
C15
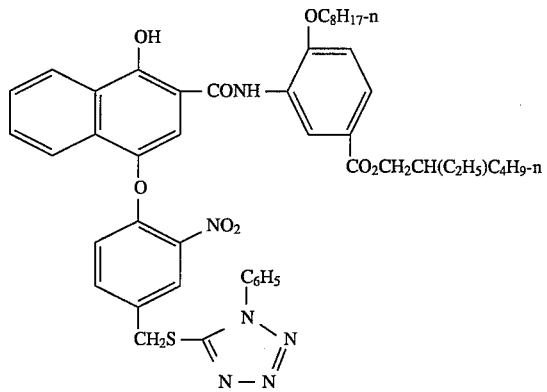
C16
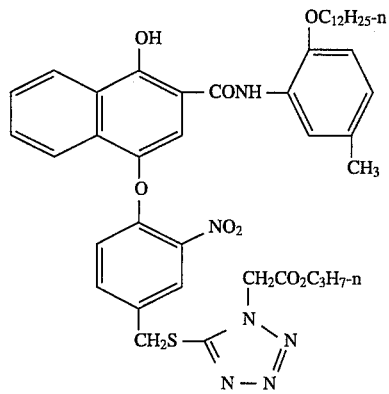
C17
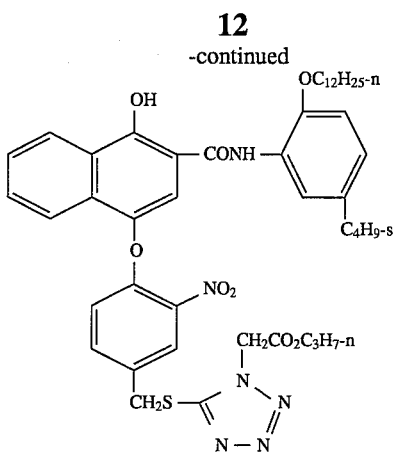
C18
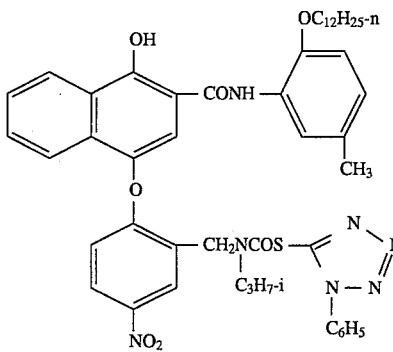
C19
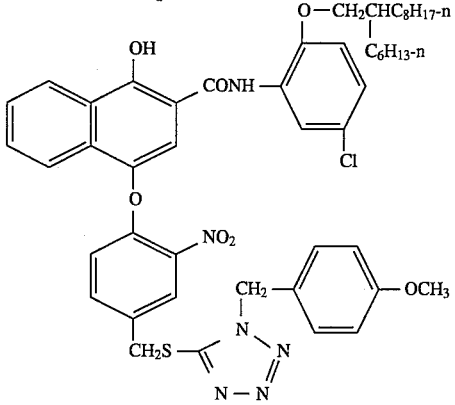
C20
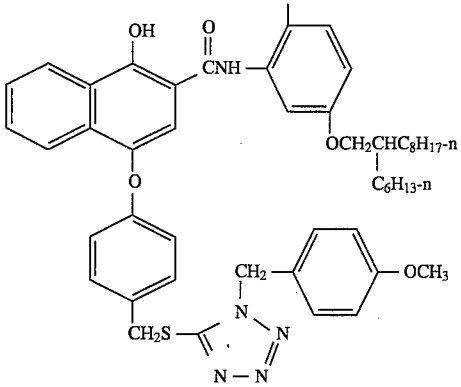
and

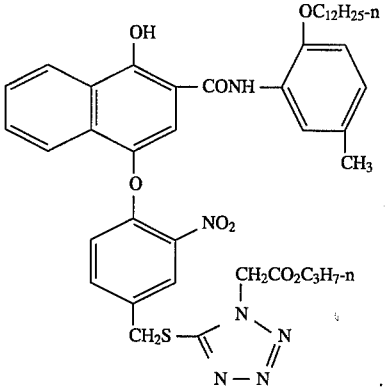

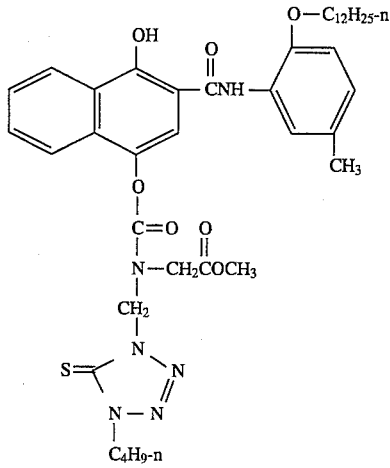

Most preferred are selected from the group consisting of:

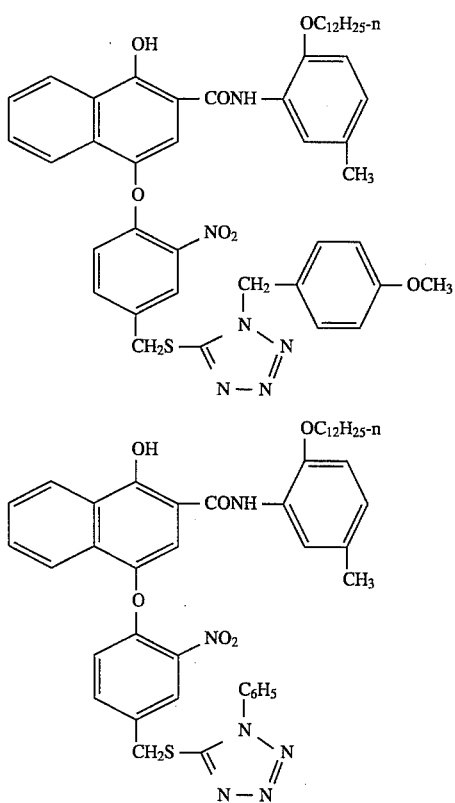

and

The photographic elements of the present invention can contain broad ranges of the above-described image-modifying couplers. Preferably, the image-modifying couplers are present in amounts between about 0.002 and about 0.40 grams per square meter. Ideally, they are present in amounts between about 0.01 and about 0.20 grams per square meter.

The development inhibitor releasing (DIAR) couplers of this invention may be used alone, or in combination with yellow or magenta image couplers or image-modifying couplers. It is desired, though, that the 2-phenylcarbamoyl-1-naphthol image-modifying couplers of this invention be used with cyan image couplers, including those of structures VIII, IX, X and XI, below:

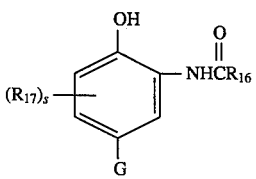  VIII

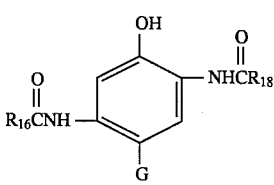  IX

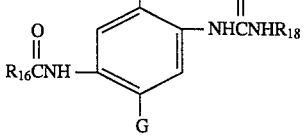  X

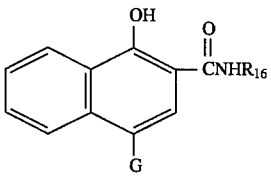  XI wherein:

s is from 0 to 3;

$R_{16}$ is a ballast group, such as an unsubstituted or a substituted alkyl group with at least 10 carbon atoms, or a substituted phenyl group with at least 10 carbon atoms;

each $R_{17}$ is individually selected from halogens, alkyl groups of 1 to 4 carbon atoms and alkoxy groups of 1 to 4 carbon atoms;

$R_{18}$ is selected from unsubstituted or substituted alkyl groups, and unsubstituted or substituted aryl groups, wherein the substituents comprise one or more electron-withdrawing groups or atoms, such as cyano, chloro, fluoro, methylsulfonyl, or trifluoromethyl; and G is hydrogen or a coupling-off group that is not photographically useful. Examples of G include chlorine, an alkoxy group, an aryloxy group, a ballasted alkylthio or arylthio group, an acyloxy group, a carbonamido group, a sulfonamido group, and a nitrogen-containing heterocyclic group, such as a pyrazolyl, an imidazolyl, a succinimido or an hydantoinyl group.

Preferred image couplers for use in combination with the 2-phenylcarbamoyl-1-naphthol image-modifying couplers of this invention are the 2-phenylureido-5-carbonamidophenol cyan dye-forming couplers of structure X, and preferably those in which $R_{18}$ is a p-cyanophenyl group and G is hydrogen or an aryloxy group. Useful weight ratios of the 2-phenylcarbamoyl-1-naphthol image-modifying couplers of this invention to image coupler are from about 0.005:1.0 to about 2.0:1.0, depending on the layer and the type of image-modifying coupler.

Specific image couplers which may be utilized in the photographic element of the present invention include:

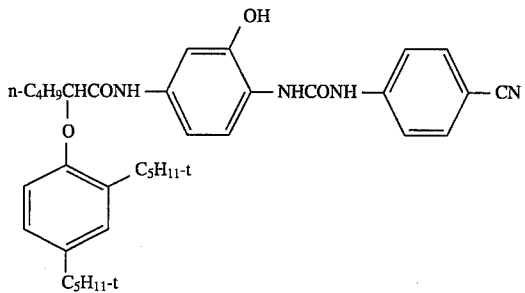

B1

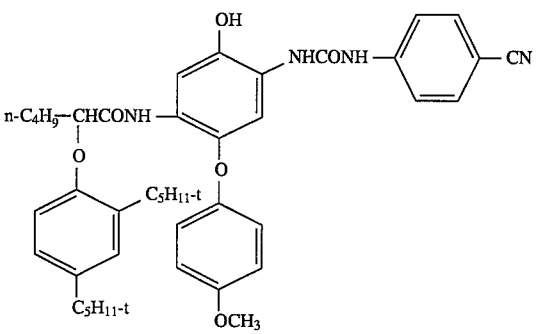

B2

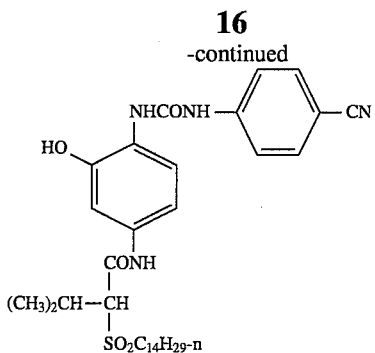

B3

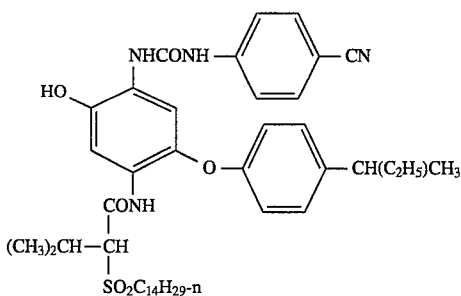

B4

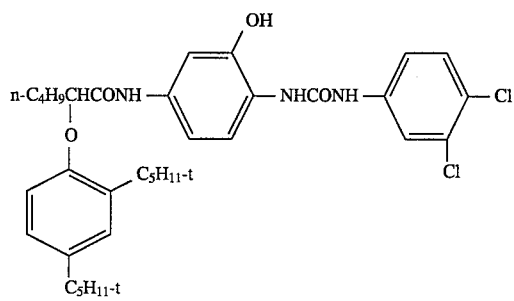

B5

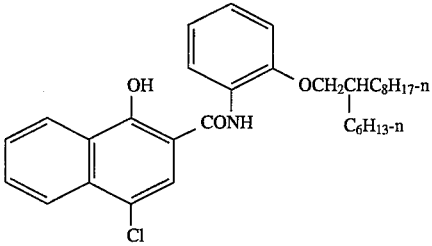

B6

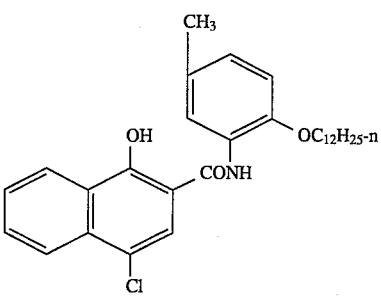

B7

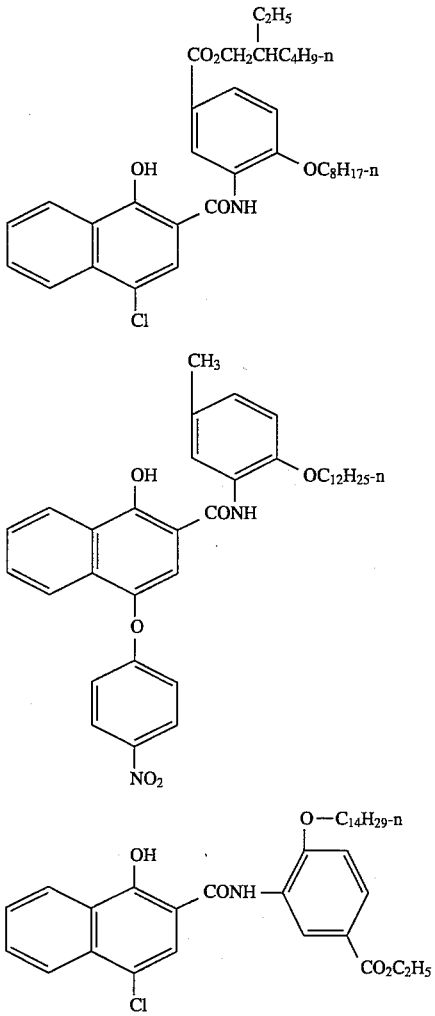

The image-modifying couplers of this invention can be utilized by dissolving them in high-boiling-temperature coupler solvents and then dispersing the organic coupler plus coupler solvent mixture as small particles in aqueous solutions of gelatin and surfactant (via milling or homogenization). Removable auxiliary organic solvents such as ethyl acetate or cyclohexanone may also be used in the preparation of such dispersions to facilitate the dissolution of the coupler in the organic phase. Coupler solvents useful for the practice of this invention include aryl phosphates (e.g. tritolyl phosphate), alkyl phosphates (e.g. trioctyl phosphate), mixed aryl alkyl phosphates (e.g. diphenyl 2-ethylhexyl phosphate), aryl, alkyl or mixed aryl alkyl phosphonates, phosphine oxides (e.g. trioctylphosphine oxide), esters of aromatic acids (e.g. dibutyl phthalate), esters of aliphatic acids (e.g. dibutyl sebecate), alcohols (e.g. 2-hexyl-1-decanol), phenols (e.g. p-dodecylphenol), carbonamides (e.g. N,N-dibutyldodecanamide or N-butylacetanalide), sulfoxides (e.g. bis(2-ethylhexyl)sulfoxide), sulfonamides (e.g. N,N-dibutyl-p-toluenesulfonamide) or hydrocarbons (e.g. dodecylbenzene). Additional coupler solvents and December 1989, Item 308119, p 993. Useful coupler:coupler solvent weight ratios range from about 1:0.1 to about 1:10, with about 1:0.2 to about 1:5.0 being preferred.

The photographic image-modifying couplers of the present invention may be employed in photographic materials in a manner well known in the photographic art. For example, a supporting substrate may be coated with a silver halide emulsion comprising a 2-phenylcarbamoyl-1-naphthol DIAR of the present invention. The 2-phenylcarbamoyl-1-naphthol image-modifying couplers may be coated with an image coupler, such as a 2-phenylureido-5-carbonamidophenol image coupler, imagewise exposed, and then developed in a solution containing a primary aromatic amine color developing agent.

The photographic elements of the present invention may be simple elements or multilayer, multicolor elements. Multicolor elements contain dye image-forming units sensitive to each of the three primary regions of the visible light spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising at least one red-sensitive silver halide emulsion layer having associated therewith at least one cyan dye-forming coupler; a magenta image-forming unit comprising at least one green-sensitive silver halide emulsion layer having associated therewith at least one magenta dye-forming coupler; and a yellow dye image-forming unit comprising at least one blue-sensitive silver halide emulsion layer having associated therewith at least one yellow dye-forming coupler. The element may contain additional layers, such as filter layers, interlayers, overcoat layers, subbing layers, and the like.

The element may also contain a transparent magnetic recording layer such as a layer containing magnetic particles on the underside of a transparent support, as in U.S. Pat. Nos. 4,279,945 and 4,302,523. Typically, the element will have a total thickness (excluding the support) of from about 5 to about 30 microns.

In the following discussion of suitable materials for use in the elements of this invention, reference will be made to *Research Disclosure*, December 1978, Item 17643, and *Research Disclosure* December 1989, Item No. 308119, both published by Kenneth Mason Publications, Ltd., Dudley Annex, 12a North Street, Emsworth, Hampshire PO10 7DQ, ENGLAND, the disclosures of which are incorporated herein by reference. This publication will be identified hereafter by the term "Research Disclosure." A reference to a particular section in "Research Disclosure" corresponds to the appropriate section in each of the above-identified Research Disclosures. The elements of the invention can comprise emulsions and addenda described in these publications and publications referenced in these publications.

The silver halide emulsions employed in the elements of this invention can be comprised of silver bromide, silver chloride, silver iodide, silver bromochloride, silver iodochloride, silver iodobromide, silver iodochlorobromide or mixtures thereof. The emulsions can include silver halide grains of any conventional shape or size. Specifically, the emulsions can include coarse, medium or fine silver halide grains. High aspect ratio tabular grain emulsions are specifically contemplated, such as those disclosed by Wilgus et al. U.S. Pat. No. 4,434,226, Daubendiek et al. U.S. Pat. No. 4,414,310, Wey U.S. Pat. No. 4,399,215, Solberg et al. U.S. Pat. No. 4,433,048, Mignot U.S. Pat. No. 4,386,156, Evans et al. U.S. Pat. No. 4,504,570, Maskasky U.S. Pat. No. 4,400,463, Wey et al. U.S. Pat. No. 4,414,306, Maskasky U.S. Pat. Nos. 4,435,501 and 4,643,966 and Daubendiek et al. U.S. Pat. Nos. 4,672,027 and 4,693,964, all of which are incorporated herein by reference. Also specifically contemplated are those silver iodobromide grains with a higher molar proportion of iodide in the core of the grain than in the periphery of the grain, such as those described in British Reference No.

1,027,146; Japanese Reference No. 54/48,521; U.S. Pat. Nos. 4,379,837; 4,444,877; 4,665,012; 4,686,178; 4,565,778; 4,728,602; 4,668,614 and 4,636,461; and in European Reference No 264,954, all which are incorporated herein by reference. The silver halide emulsions can be either monodisperse or polydisperse as precipitated. The grain size distribution of the emulsions can be controlled by silver halide grain separation techniques or by blending silver halide emulsions of differing grain sizes.

Sensitizing compounds, such as compounds of copper, thallium, lead, bismuth, cadmium and Group VIII noble metals, can be present during precipitation of the silver halide emulsion.

The emulsions can be surface-sensitive emulsions, i.e., emulsions that form latent images primarily on the surface of the silver halide grains; or internal latent image-forming emulsions, i.e., emulsions that form latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

The silver halide emulsions can be surface-sensitized, and noble metal (e.g., gold), middle chalcogen (e.g., sulfur, selenium, or tellurium) and reduction sensitizers, employed individually or in combination, are specifically contemplated. Typical chemical sensitizers are listed in *Research Disclosure* Item 308119, cited above, Section III.

The silver halide emulsions can be spectrally sensitized with dyes from a variety of classes, including the polymethine dye class, which includes the cyanines, merocyanines, complex cyanines and merocyanines (i.e., tri-tetra-, and polynuclear cyanines and merocyanines), oxonols, hemioxonols, stryryls, merostyryls, and streptocyanines. Illustrative spectral sensitizing dyes are disclosed in *Research Disclosure* Item 308119, cited above, Section IV.

Suitable vehicles for the emulsion layer and other layers of elements of this invention are described in *Research Disclosure*, Item 308119, Section IX and the publications cited therein.

Besides the 2-phenylcarbamoyl-1-naphthol DIAR couplers described herein, the elements of this invention can include additional couplers as described in *Research Disclosure*, Section VII, paragraphs D, E, F, and G and the publications cited therein. The additional couplers can be incorporated as described in *Research Disclosure*, Section VII, paragraph C, and the publications cited therein.

The photographic elements of this invention can contain brighteners (*Research Disclosure*, Section V), antifoggants and stabilizers (*Research Disclosure*, Section VI), antistain agents and image dye stabilizers (*Research Disclosure*, Section VII, paragraphs I and J), light absorbing and scattering materials (*Research Disclosure*, Section VIII), hardeners (*Research Disclosure*, Section X), coating aids (*Research Disclosure*, Section XI), plasticizers and lubricants (*Research Disclosure*, Section XII), antistatic agents (*Research Disclosure*, Section XIII), matting agents (*Research Disclosure*, Section XII and XVI) and development modifiers (*Research Disclosure*, Section XXI.

The photographic elements can be coated on a variety of supports as described in *Research Disclosure*, Section XVII and the references described therein.

The photographic elements of the invention can be exposed to actinic radiation, typically in the visible region of the spectrum, to form a latent image as described in *Research Disclosure*, Section XVIII, and then processed to form a visible dye image as described in *Research Disclosure*, Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylenediamines. Especially preferred are 4-amino-3-methyl-N,N-diethylaniline hydrochloride, 4-amino-3-methyl-N-ethyl-N-(β-methanesulfonamidoethyl)-aniline sulfate hydrate, 4-amino-3-methyl-N-ethyl-N-(β-hydroxyethyl)-aniline sulfate, 4-amino-3-(β-methanesulfonamidoethyl)-N,N-diethylaniline hydrochloride, and 4-amino-N-ethyl-N-(β-methoxyethyl)-m-toluidine di-p-toluenesulfonic acid. With negative-working silver halide, the processing step described above provides a negative image. The described elements are preferably processed in the known C-41 color process as described in, for example, the British Journal of Photography Annual, 1988, pages 196–198. To provide a positive (or reversal) image, the color development step can be preceded by development with a non-chromogenic developing agent to develop exposed silver halide, but not from dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver or silver halide, washing, and drying.

Preparation of the 2-phenylcarbamoyl-1-naphthol couplers of this invention is illustrated by the following synthetic example.

Synthesis Example A: Synthesis of the inventive DIAR coupler C2 is shown schematically below and described in detail in the subsequent paragraphs.

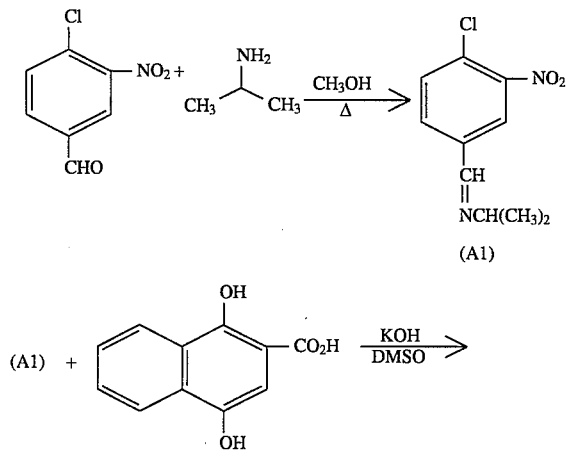

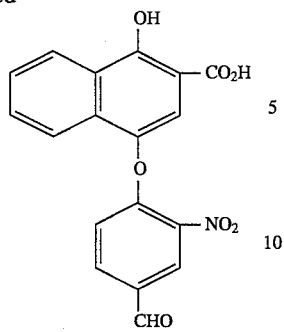

(A2)

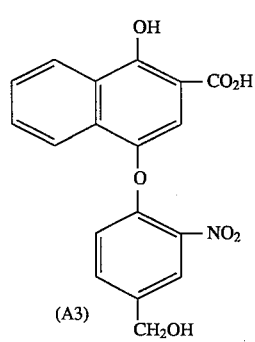

(A3)

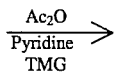

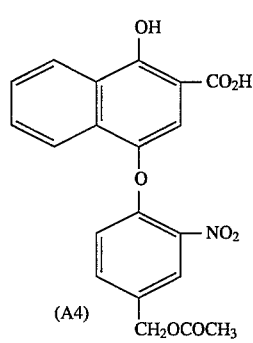

(A4)

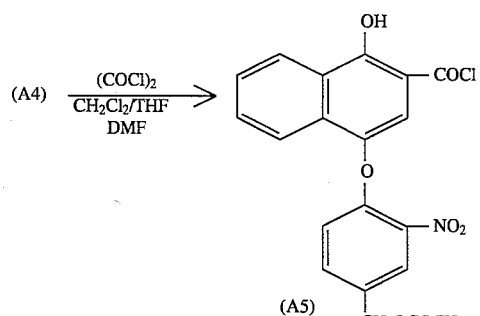

(A5)

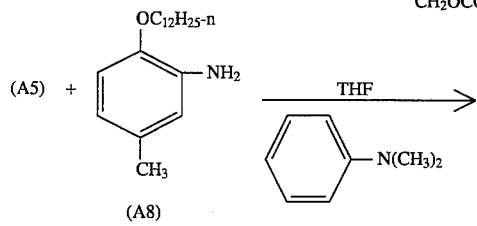

(A8)

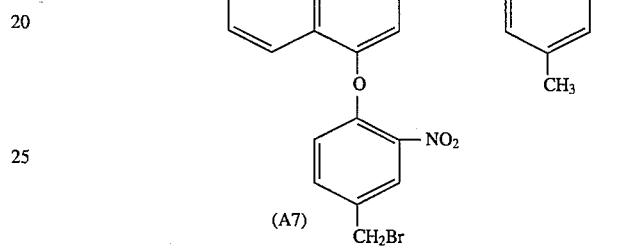

(A6)

(A6) $\xrightarrow{\text{HBr/HOAc}}$

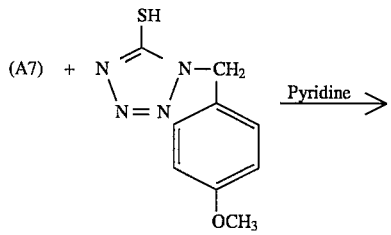

(A7)

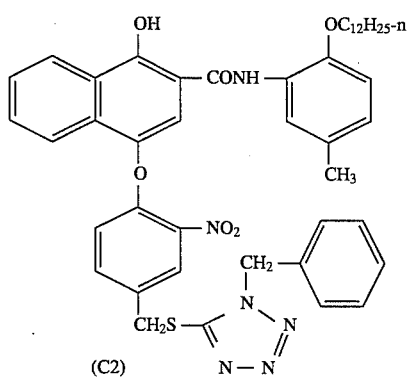

(C2)

Intermediate (A4) was first prepared as outlined in the above scheme. (A1) was prepared by refluxing 4-chloro-3-nitrobenzaldeyhde with isopropylamine in methanol. (A1) was then reacted with 1,4-dihydroxy-2-naphthoic acid in the presence of base to form (A2). Reduction of the aldehyde in (A2) with sodium borohydride gave (A3), which was acetylated with acetic anhydride in pyridine. Subsequent treatment of the product mixture with tetramethylguanidine (TMG) gave (A4).

Compound (A5): Compound (A4)(46.0 g, 0.12 mol) was slurried in a solution containing 300 mL of dichloromethane, 100 mL of tetrahydrofuran and two drops of N,N-dimethylformamide. Oxalyl chloride (11.5 mL, 0.13 mol) was added dropwise at room temperature. All of the (A4) dissolved within 15 min. After the evolution of gas had ceased the solvents were removed on a rotary evaporator, yielding (A5) as a semi-solid.

Compound (A6): (A5) was immediately dissolved in 300 mL of tetrahydrofuran. While stirring at room temperature, a solution of 33.7 g (0.12 mol) of compound (A8) and 16.0 mL (0.13 mol) of N,N-dimethylaniline in 100 mL of tetrahydrofuran was added in one portion. The reaction mixture was stirred overnight at room temperature and then poured into a dilute solution of hydrochloric acid and extracted with ethyl acetate. The extract was dried over magnesium sulfate and filtered. The filtrate was concentrated to an oil, dissolved in toluene and chromotagraphed on silica gel using 85:15 ligroin:ethyl acetate as the eluant. On evaporation of the eluant, an oil was obtained, which crystallized on stirring in an ether/ligroin mixture yielding 35.4 g (44%) of (A6).

Compound (A7): A solution of 31% hydrogen bromide in acetic acid (32 mL, 0.42 mol) was added to a slurry of 35.4 g (0.053 mol) of (A6) in 250 mL of acetic acid, and the mixture was heated to 80° C. for two hours. All of the (A6) dissolved. The reaction mixture was cooled to room temperature, poured into water and extracted with ethyl acetate. The combined extract was concentrated to dryness, and the residue was diluted with 1.5L of ligroin and cooled in an ice acetone bath. The product (A7) crystallized, yielding 28.0 g (76%) of a yellow solid.

Compound C2: Compound (A7) (28.0 g, 0.041 mol) and 1-(4-methoxybenzyl)-2-tetrazoline-5-thione (9.0 g, 0.041 mol) were added to 250 mL of pyridine. After stirring the mixture at room temperature for 1.5 hours, tlc indicated that all of (A7) had reacted. The mixture was than poured into a dilute hydrochloric acid solution and extracted with ethyl acetate. The extract was washed successively with brine, saturated sodium bicarbonate, brine and a 10% hydrochloric acid solution and then dried over magnesium sulfate. The mixture was filtered, and the filtrate was concentrated to give an oil. The oil was dissolved in toluene and chromotographed on silica gel using 85:15 ligroin:ethyl acetate as the eluant. The oil obtained on evaporation of the eluant was crystallized in ether/ligroin, yielding 13.0 g (38%) of C2 as a yellow solid (MP= 104°–107° C.). The product structure was confirmed by NMR spectroscopy and elemental analysis.

The advantages of the coupler compositions of this invention and of the color photographic materials comprising such couplers are further illustrated by the following comparative examples.

EXAMPLES

In the following examples, coupler solvent S1 refers to tritolyl phosphate (mixed isomers), coupler solvent S2 is dibutyl phthalate, coupler solvent S3 is 1,4-cyclohexylenedimethylene bis(2-ethylhexanoate), coupler solvent S4 is N,N-diethyldodecanamide, coupler solvent S5 is N-butylacetanilide and coupler solvent S6 is N,N-dibutyldodecanamide.

Example 1. Illustration of the Advantageous Properties of the Image-Modifying Couplers of this Invention in a Simplified Test Format.

In order to rapidly evaluate the 2-phenylcarbamoyl-1-naphthol image-modifying couplers of this invention, simple testing procedures were developed for initial comparisons. For these tests, each image-modifying coupler or, in some cases, a four-equivalent parent coupler was coated on a transparent acetate support as a single layer in a gelatin binder. The hardened films were then immersed in a solution containing 4-amino-3-methyl-N-ethyl-N-(β-hydroxyethyl)aniline sulfate (the developer used in the C-41 process) and potassium ferricyanide buffered at a pH of 10. The ferricyanide oxidized the developer, which then reacted with the coupler to form dye. The dye absorption spectrum was then measured on a spectrophotometer. Samples were stored at low temperatures and spectra were remeasured to determine the extent of dye crystallization. The extent of reduction to leuco cyan dye (LCD formation) in a simulated seasoned bleach was also determined for the film samples using the procedures described below. In certain instances, the testing procedures were carried out on coatings of the corresponding four-equivalent parent coupler.

The specific dispersion preparation and coating procedures used for the DIAR couplers are illustrated below. An oil phase consisting of 0.10 g of the DIAR coupler, 0.20 g of the coupler solvent S1, and 1.6 mL of ethyl acetate auxiliary solvent, was dispersed in an aqueous phase containing 20.2 mL of water, 1.0 g of gelatin, and 0.1 g of the sodium salt of tri-isopropylnaphthylenesulfonic acid (a surfactant) by passing the mixture through a colloid mill in a manner known in the art. Formaldehyde (0.008 g) was added to the dispersion which was then coated on a cellulose acetate support. The aim DIAR laydown was 0.45 g/sq m and the aim gelatin laydown was 4.5 g/sq m. The ethyl acetate evaporated upon coating.

To convert the couplers to dye, the hardened films were immersed for two minutes in a pH=10 borate buffer solution containing 2.0 g/L of 4-amino-3-methyl-N-ethyl-N-(β-hydroxyethyl)-aniline sulfate, 0.25 g/L of sodium sulfate, and 12.0 g/L of potassium ferricyanide. This simulated the chromogenic development in photographic materials. The dye-containing films were then immersed in a 2% acetic acid solution for one minute and then washed for five minutes at 27° C. After the films were dry, the spectra were measured. The spectral absorption maxima (lambda max values) are reported in the tables below. Most film samples had a density of approximately 1.5 at the absorption maximum near 700 nm.

To evaluate the propensity for dye crystallization on cold storage, samples were placed in a freezer at −18° C. for 48 hr. The absorption spectra were then remeasured on a spectrophotometer. The density loss percentages at the absorption maxima due to dye crystallization are listed in the tables below.

To probe the propensity for reduction of cyan dye to the leuco form in seasoned bleaches (LCD formation), or in bleaches of weak oxidizing strength, a test was designed to simulate the bleaching step of a photographic process, such as the C-41 process. After recording the absorption spectra, the dye-containing films were placed for three minutes in a solution consisting of 50 mL of water, 50 mL of fresh Bleach II used in the C-41 process, 2.0 g of ferrous sulfate heptahydrate, 2.5 g of the dipotassium salt of (ethylenedinitrilo)-tetraacetic acid (EDTA) and 1.5 mL of ammonium hydroxide reagent. The pH of the solution was adjusted to 4.75 with acetic acid prior to immersion of the film samples. This procedure simulated the early stages of the C-41 bleach process, in which ferrous ion concentrations are quite high due to reduction of iron EDTA upon oxidation of developed silver. The film samples were then placed for four minutes in a solution consisting of 100 mL of fresh C-41 Bleach II, 1.0 g/L of ferrous sulfate heptahydrate and 0.2 g/L of dipotassium EDTA adjusted to a pH of 4.75. This simulated the ferrous ion levels and acidity of seasoned bleaches actually observed in seasoned processing solutions encountered in trade laboratories. The films were then washed and dried, and their spectra were remeasured. The percentage losses in density at lambda max due to leuco cyan dye formation are also listed in the tables below. Initial densities were approximately 1.5.

Test data for example 2-phenylcarbamoyl-1-naphthol DIAR couplers of this invention are provided in Table IA. Structures of comparative couplers D1 through D-4 are given below.

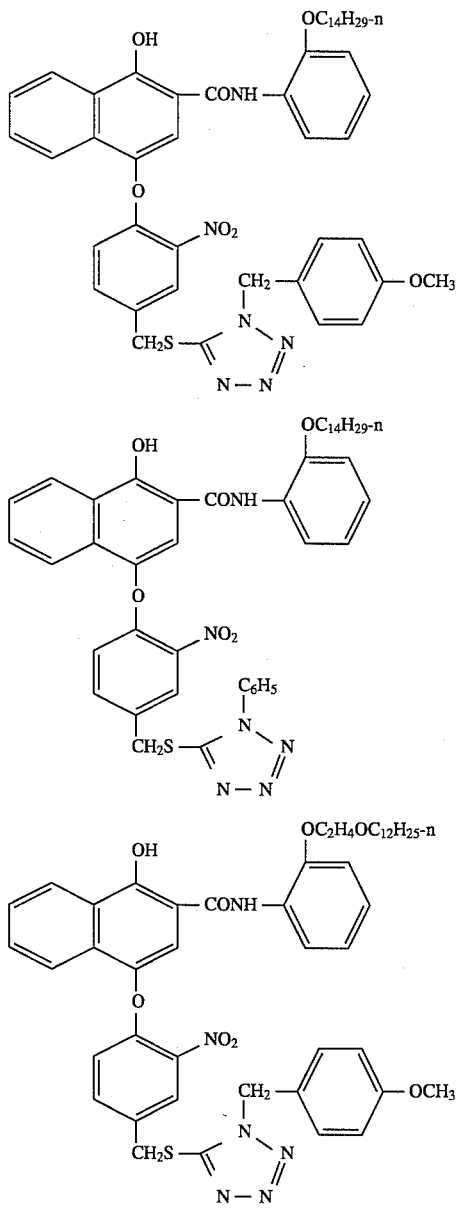

-continued

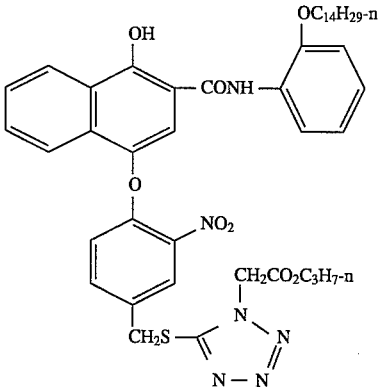

TABLE IA

| Coupler | Coupler Solvent | Weight Ratio[1] | Lambda Max (nm)[2] | Density Loss % at Lambda Max 48 hr @ −18° C.[3] | Density Loss % in Simulated Seasoned Bleach[4] (LCD Test) |
|---|---|---|---|---|---|
| 1 D1 | S1 | 1:2 | 701 | 82.1 | 1.7 |
| 2 D2 | S5 | 1:2 | 574 | Dye Crystallized on Processing | |
| 3 D3 | S1 | 1:2 | 701 | 12.0 | 0.5 |
| 4 D3 | S2 | 1:2 | 698 | 81.0 | 1.9 |
| 5 D3 | S5 | 1:2 | 692 | 76.2 | 20.8* |
| 6 D4 | S1 | 1:2 | 701 | 81.0 | 2.3 |
| 7 C1 | S1 | 1:2 | 701 | 0.0 | 0.6 |
| 8 C1 | S2 | 1:2 | 698 | 0.0 | 2.3 |
| 9 C1 | S5 | 1:2 | 693 | 0.0 | 2.0 |
| 10 C2 | S1 | 1:2 | 700 | 0.0 | 0.4 |
| 11 C2 | S5 | 1:2 | 690 | 0.0 | 1.9 |
| 12 C3 | S1 | 1:2 | 706 | 0.0 | 0.7 |
| 13 C6 | S1 | 1:2 | 701 | 0.0 | 1.0 |
| 14 C6 | S5 | 1:2 | 693 | 0.0 | 2.1 |
| 15 C7 | S1 | 1:2 | 708 | 0.0 | 0.7 |
| 16 C8 | S1 | 1:2 | 706 | 0.0 | 1.6 |
| 17 C10 | S1 | 1:2 | 704 | 0.0 | 1.0 |
| 18 C13 | S5 | 1:2 | 693 | 0.0 | 1.5 |
| 19 C14 | S5 | 1:2 | 691 | 0.0 | 1.0 |
| 20 C16 | S1 | 1:2 | 699 | 0.0 | 1.0 |
| 21 C17 | S1 | 1:2 | 701 | 0.0 | 1.2 |

[1]Coupler to coupler solvent weight ratio
[2]Spectral absorbtion maxima
[3]Density loss percentages at the absorption maxima due to dye crystallization
[4]Density loss percentages at the absorption maxima due to leuco cyan dye formation
*Some dye crystallization occurred during the LCD test.

From the data in Table IA, it is evident that all of the comparative DIAR couplers D1 through D4 yield dyes which undergo a large loss in red density on cold storage due to crystallization. For example, the dye derived from the comparative coupler D1 shows a particularly large loss (82.1%) in red density upon storage at −18° C. for 48 hours. Data for the other comparative couplers indicates that they too exhibit substantial loss in density due to dye crystallization.

In marked contrast to the comparative couplers, the couplers of this invention, C1, C2, C3, C6, C7, C8, C10, C13, C14, C16 and C17 all yield dyes that show no density loss on cold storage and no more than 2.3 percent density loss in the LCD test. C1, for example, shows no density loss due to crystallization in coupler solvents S1 and S2. It also shows no more than 2.3 percent loss due to leuco cyan dye formation in the same coupler solvents.

Couplers C1, C2, C6, C10, C13, C14, C16 and C17 are the most preferred couplers of those tested. This is because in coupler solvent S1, they yield dyes with lambda values at, or near, 700 nm. Couplers which yield dyes with lambda max values significantly above 700 nm are somewhat bathochromic. As a result, they are less desirable for optimum printing characteristics in color negative materials. This is because a typical color paper onto which a negative is printed has a maximum sensitivity in the region of about 700 nm. Dyes that have an absorption maximum between about 703 nm and 709 nm, though effective, do not modulate light as efficiently in the region of maximum paper sensitivity as dyes which have absorption maxima closer to 700 nm. Dyes that have an absorption maximum above about 709 nm are particularly inefficient and are thus less preferred.

Table IB provides comparative data for a variety of types of four-equivalent 2-phenylcarbamoyl-1-naphthol couplers to illustrate the shortcomings of dyes derived from parent structures that are outside the scope of the claimed invention. Only couplers E8 and E14 have the substituents, and locations thereof, to place themselves (with a switched or timed inhibitor moiety) and the dyes they yield within the scope of invention; E8 and E14 yield dyes with suitable resistance to crystallization and leuco dye formation. The structures of couplers E1 through E14 are given below.

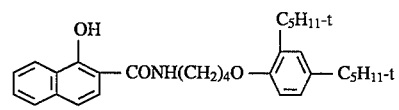  E1

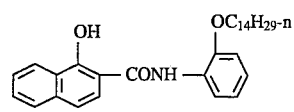  E2

  E3

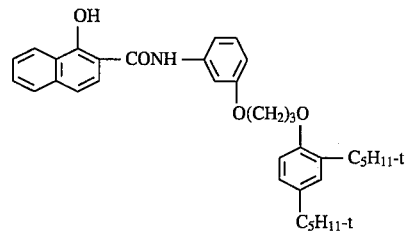  E4

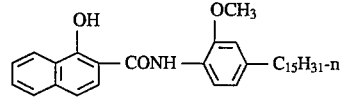  E5

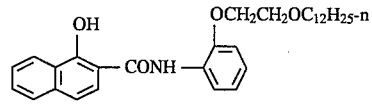  E6

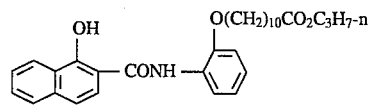  E7

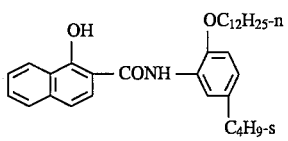  E8

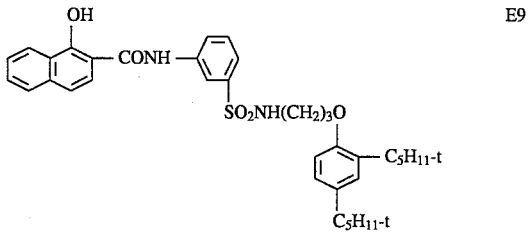  E9

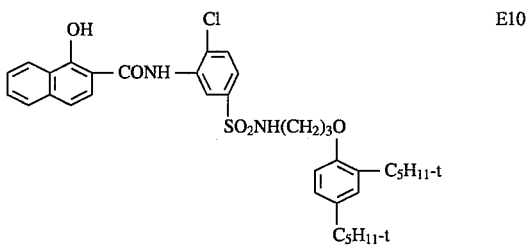  E10

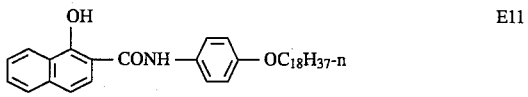  E11

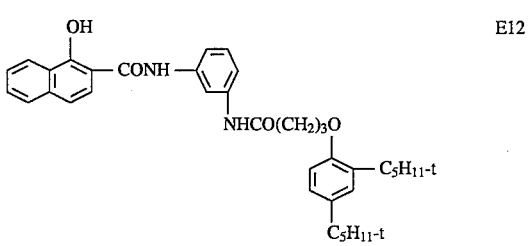  E12

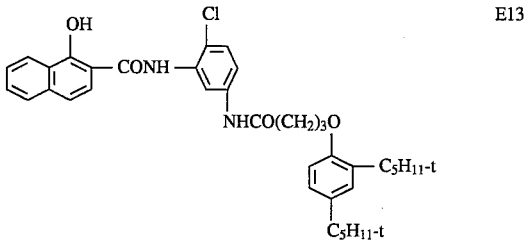  E13

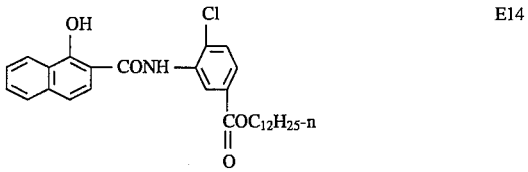  E14

TABLE IB

| Coupler | Coupler Solvent | Weight Ratio[1] | Lambda Max (nm)[2] | Density Loss % at Lambda Max 48 hr @ −18° C.[3] | Density Loss % in Simulated Seasoned Bleach[4] (LCD Test) |
|---|---|---|---|---|---|
| 1 E1 | S1 | 1:2 | 693 | 0.0 | 17.2 |
| 2 E2 | S1 | 1:2 | 700 | 81.4 | 5.3* |
| 3 E3 | S1 | 1:2 | 694 | 1.2 | 15.7 |

TABLE IB-continued

| Coupler | Coupler Solvent | Weight Ratio[1] | Lambda Max (nm)[2] | Density Loss % at Lambda Max 48 hr @ −18° C.[3] | Density Loss % in Simulated Seasoned Bleach[4] (LCD Test) |
| --- | --- | --- | --- | --- | --- |
| 4 E4  | S1 | 1:2 | 710 | 0.3  | 6.0  |
| 5 E5  | S1 | 1:2 | 700 | 16.4 | 2.6  |
| 6 E6  | S2 | 1:2 | 698 | 82.1 | 2.2  |
| 7 E7  | S1 | 1:2 | 702 | 54.6 | 1.6  |
| 8 E8  | S1 | 1:2 | 701 | 0.0  | 1.4  |
| 9 E8  | S2 | 1:2 | 698 | 0.0  | 2.3  |
| 10 E8 | S6 | 1:4 | 697 | 0.0  | 3.1  |
| 11 E9 | S1 | 1:2 | 720 | 0.0  | 7.4  |
| 12 E10| S1 | 1:2 | 724 | 28.9 | 1.3  |
| 13 E11| S6 | 1:4 | 704 | 54.2 | 10.9 |
| 14 E12| S1 | 1:2 | 710 | 1.1  | 7.6  |
| 15 E13| S1 | 1:2 | 711 | 0.1  | 1.1  |
| 16 E14| S1 | 1:2 | 715 | 0.8  | 0.8  |

[1] Coupler to coupler solvent weight ratio
[2] Spectral absorbtion maxima
[3] Density loss percentages at the absorption maxima due to dye crystallization
[4] Density loss percentages at the absorption maxima due to leuco cyan dye formation
*Dye crystallization during the LCD test procedure contributes to the red density losses for this film.

According to the data in Table IB couplers E2, E5, E6, E7, E10 and E11 all yield dyes that show substantial density losses at lambda max due to dye crystallization on cold storage. Couplers E1, E3, E4, E9, E11 and E12 all yield dyes that show substantial (greater than 5%) density losses at lambda max in the simulated seasoned bleach LCD test. Couplers E4, E9, E10, E12 and E13 also yield dyes with hues that are generally bathochromic (lambda max greater than 709 nm) in S1. Couplers E8 and E14, which are four-equivalent analogs (absent a switched or timed inhibitor moiety) of the image-modifying couplers of this invention, yield dyes that are resistant to crystallization on cold storage and to reduction in a seasoned bleach.

Example 2. Evaluation of the 2-Phenylcarbamoyl-1-Naphthol Image-Modifying Couplers of this Invention in a Photographic Element.

The coating format in the diagram below was used for evaluation of the DIAR couplers of this invention in a photographic element. Construction of the element was done by conventional methods known in the art, wherein the DIAR couplers were coated at 0.861 mmol/sq m together with 0.646 g/sq m of silver as a 0.3 micrometer cubic silver bromochloride (1% Br) emulsion.

---

2.69 g/sq m Gelatin (Overcoat)
0.129 g/sq m Bis(vinylsulfonylmethyl) Ether Hardener
3.77 g/sq m Gelatin
0.861 mmol/sq m DIAR (e.g. 0.73 g/sq m D1)
Coupler Solvent @ 1:2 or 1:4 Coupler:Solvent by Weight
0.646 g/sq m Silver as a Silver Bromochloride (1% Br) Emulsion
Cellulose Acetate Butyrate Support

---

After hardening, the films were exposed through a step tablet on a 1B sensitometer and then subjected to a KODAK FLEXICOLOR® C-41 process as described in more detail below. To evaluate the propensity for leuco cyan dye formation in a seasoned bleach, 35 mm film strips were exposed and slit in half. Both halves were then processed at the same time in C-41 developer, and placed in a stop bath to eliminate any variability due to continued coupling. Then, one half was processed in fresh C-41 Bleach II and the other half was processed in a simulated seasoned bleach (Bleach B). Bleach B consisted of fresh Bleach II to which was added 10.0 g/L of ferrous sulfate heptahydrate and 2.0 g/L of dipotassium EDTA dihydrate with the the bleach pH adjusted to 4.75. During processing in Bleach B, agitation was provided by nitrogen bubbling (as opposed to air bubbling for Bleach II) to minimize air oxidation of ferrous ion to ferric ion. Status M red densities(Dr) were measured versus exposure for the samples processed in fresh Bleach II and in simulated seasoned Bleach B. Status M red densities (Dr) were also measured for a set of processed film samples before and after cold storage for 48 hr at −18° C. Density losses were determined from an initial density of 1.0. Test results are summarized in Table II.

C-41 PROCESSING SOLUTIONS AND CONDITIONS

| Solution | Processing Time | Agitation Gas |
| --- | --- | --- |
| C-41 Developer | 3' 15" | Nitrogen |
| Stop Bath | 30" | Nitrogen |
| A) Fresh Bleach II | 3' | Air |
| or B) Seasoned Bleach B | 3' | Nitrogen |
| Wash | 1' | None |
| C-41 Fix | 4' | Nitrogen |
| Wash | 4' | None |
| PHOTO-FLO™ | 30" | None |
| Processing Temperature | 100° F. | |

TABLE II

| Coupler | Coupler Solvent | Weight Ratio[1] | Dr Loss % (Status M) in 48 hr @ −18° C.[2] | Dr (Bleach B)− Dr (Bleach II) at Dr = 1.0[3] |
| --- | --- | --- | --- | --- |
| 1 D1  | S1 | 1:2 | 15.3 | −0.04 |
| 2 D2  | S1 | 1:2 | 10.2 | −0.02 |
| 3 D3  | S2 | 1:2 | 11.6 | −0.06 |
| 4 D4  | S1 | 1:2 | 13.8 | −0.04 |
| 5 C1  | S1 | 1:2 | 0.0  | −0.02 |
| 6 C1  | S2 | 1:2 | 0.0  | −0.03 |
| 7 C2  | S1 | 1:2 | 0.0  | −0.04 |
| 8 C8  | S1 | 1:2 | 0.0  | −0.07 |
| 9 C13 | S1 | 1:2 | 0.0  | −0.05 |
| 10 C16| S1 | 1:2 | 0.0  | −0.00 |

[1] Coupler to coupler solvent weight ratio
[2] Red density loss percentages due to dye crystallization.
[3] Red density loss due to the leuco cyan dye formation As is illustrated by the data in Table II, only the couplers of this invention yield dyes that do not lose red density on cold storage, and that undergo minimal loss of red density in a seasoned bleach solution. All of the comparative couplers yield dyes which show severe red density losses after 48 hr at −18° C. due to dye crystallization. The inventive films, by contrast, show no such red density losses on cold storage. Further, they exhibit almost no density loss due to leuco cyan dye formation.

In the course of determining the couplers of the present invention, it was found that other types of novel two- (or four) equivalent 2-phenylcarbamoyl-1-naphthol image-modifying couplers also exhibit a resistance to leuco cyan dye formation and crystallization at low temperatures. These other image-modifying couplers, which are other than DIAR couplers, include bleach accelerator releasing couplers (BARCS), development inhibitor releasing couplers having no timing groups or switches (DIR couplers), and masking couplers. The BARCs and DIR couplers preferably have the structure:

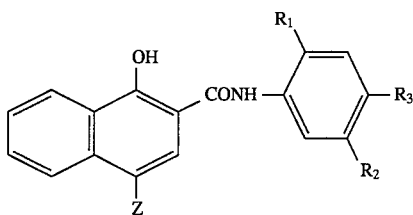

wherein:

$R_1$ is selected from an alkoxy group, a phenoxy group and halogen;

$R_2$ is selected from the group consisting of an alkyl group, a phenyl group, an alkoxy group, a halogen, and an alkoxycarbonyl group;

$R_3$ is selected from hydrogen, and an alkyl group;

$R_1$, $R_2$, and $R_3$ together contain at least 3 carbon atoms; and

Z is a bleach accelerator group or a development inhibitor group.

The masking couplers preferably have the structure:

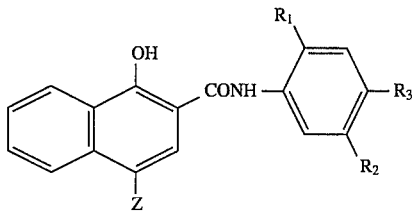

wherein:

$R_1$ is selected from an alkoxy group, a phenoxy group, and halogen;

$R_2$ is selected from the group consisting of an alkyl group, a phenyl group, an alkoxy group, an alkoxycarbonyl group, and a halogen;

$R_3$ is selected from hydrogen, and an alkyl group;

$R_1$, $R_2$, and $R_3$ together contain at least 3 carbon atoms; and

Z is a coupling off group having the formula

—A—B—N=N—D wherein:

A represents a divalent linking group which releases from the coupler upon reaction of the coupler with oxidized developer to cleave Z from the remainder of the coupler;

B is a divalent aromatic group; and

D is an aryl group containing at least one sulfonate or carboxyl group.

In the preferred embodiments of the present invention, any or all of the above-described BARCs, DIR couplers, and masking couplers, are combined with the novel two-equivalent 2-phenylcarbamoyl-1-naphthol image-modifying couplers of the present invention, and incorporated into a photographic element. Preferably, the same four equivalent parent coupler is utilized as the basis for all the cyan dye forming DIR couplers, DIAR couplers, BARCs, and masking couplers.

The invention has been described in detail with particular reference to preferred embodiments thereof but it will be understood that variations and modifications can be effected within the spirit and scope of the invention.

What is claimed:

1. A photographic element comprising a support bearing (a) at least one silver halide emulsion and (b) at least one cyan dye-forming 2-phenylcarbamoyl-1-naphthol image-modifying coupler having the structure:

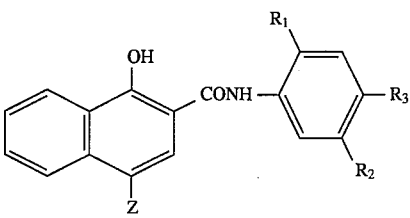

wherein:

$R_1$ is selected from an alkoxy group, a phenoxy group and halogen;

$R_2$ is selected from the group consisting of an unsubstituted or substituted alkyl group, an unsubstituted or substituted phenyl group, an unbranched unsubstituted alkoxy group, a halogen, and an alkoxycarbonyl group; with the proviso that when $R_2$ is an alkoxycarbonyl group or halogen, $R_1$ is an alkoxy or a phenoxy group;

$R_3$ is selected from hydrogen, and an alkyl group;

$R_1$, $R_2$, and $R_3$ together contain at least 3 carbon atoms; and

Z is a development inhibitor releasing group having the structure

$$\begin{array}{c} | \\ (\text{TIME})_w \\ | \\ \text{IN} \end{array}$$

wherein:

IN is a development inhibitor moiety;

TIME is a timing group or switch capable of releasing the development inhibitor moiety by means of intramolecular nucleophilic displacement reaction or electron transfer reaction down a conjugated chain; and w is 1, 2, or 3.

2. A photographic element according to claim 1, wherein Z is selected from the structures:

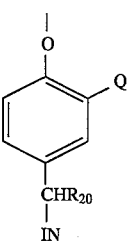

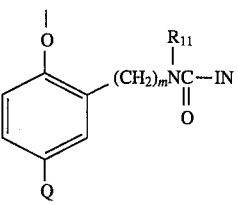

-continued

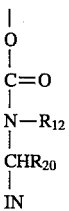

wherein:

m is 0 or 1;

Q is an electron withdrawing group;

$R_{11}$ is selected from an alkyl group containing from 1 to 8 carbon atoms, and a phenyl group;

$R_{12}$ is an alkyl group;

$R_{20}$ is selected from hydrogen and an alkyl group; and

IN is a development inhibitor moiety.

3. A photographic element according to claim 2 wherein $R_1$ is selected from an unsubstituted unbranched alkoxy group, and a substituted alkoxy group having less than six carbon atoms.

4. A photographic element according to claim 2 wherein $R_1$, $R_2$, and $R_3$, together contain at least 9 carbon atoms.

5. A photographic element according to claim 4 wherein $R_1$ is an unsubstituted, unbranched alkoxy group, $R_2$ is an alkoxycarbonyl group, and $R_3$ is hydrogen.

6. A photographic element according to claim 5 wherein $R_1$ is an n-octyloxy group and $R_2$ is a 2-ethylhexoxycarbonyl group.

7. A photographic element according to claim 2 wherein IN is selected from the structures:

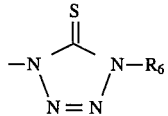

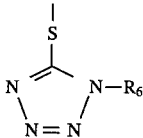

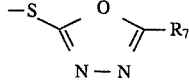

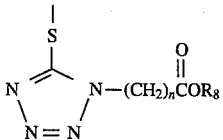

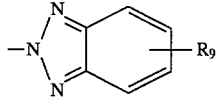

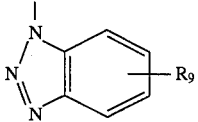

wherein:

$R_6$ is selected from the group consisting of an alkyl group containing from 1 to 8 carbon atoms, a benzyl group, and a phenyl group;

$R_7$ is $R_{13}$ or $SR_{13}$, where $R_{13}$ is selected from the group consisting of an alkyl group containing from 1 to 8 carbon atoms, a benzyl group, and a phenyl group;

$R_8$ is an alkyl group containing 1 to 5 carbon atoms;

$R_9$ is selected from the group consisting of hydrogen, halogen, alkoxy, phenyl, —$COOR_{10}$ and $NHCOOR_{10}$, wherein $R_{10}$ is an alkyl group, an alkylthio group, or a phenyl group; and n is from 1 to 3.

8. A photographic element according to claim 2 wherein Z has the structure:

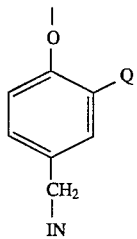

wherein Q is a nitro group, and IN has the structure:

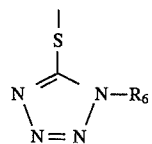

wherein $R_6$ is selected from phenyl and p-methoxybenzyl.

9. A photographic element according to claim 2 wherein when $R_1$ is an alkoxy group and $R_2$ is an alkoxycarbonyl group, IN is a development inhibitor moiety other than a 1-phenyl-1H-tetrazole-5-thio group or a 2-carboxy-phenyl-thio group.

10. A photographic element according to claim 2 wherein Z has the structure:

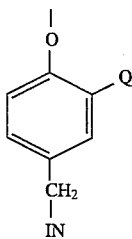

wherein Q is a nitro group and IN has the structure:

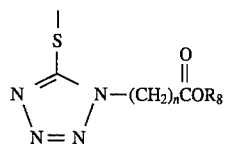

wherein n is 1; and $R_8$ is propyl.

11. A photographic element according to claim 7 wherein the image-modifying releasing coupler is selected from the group consisting of

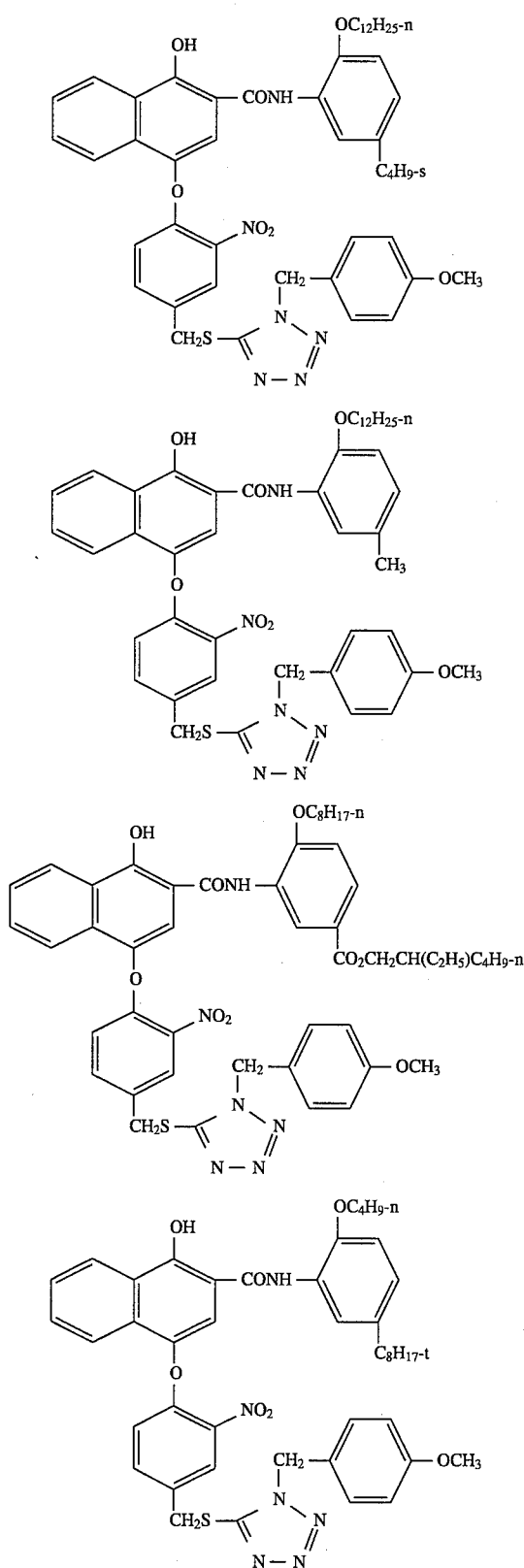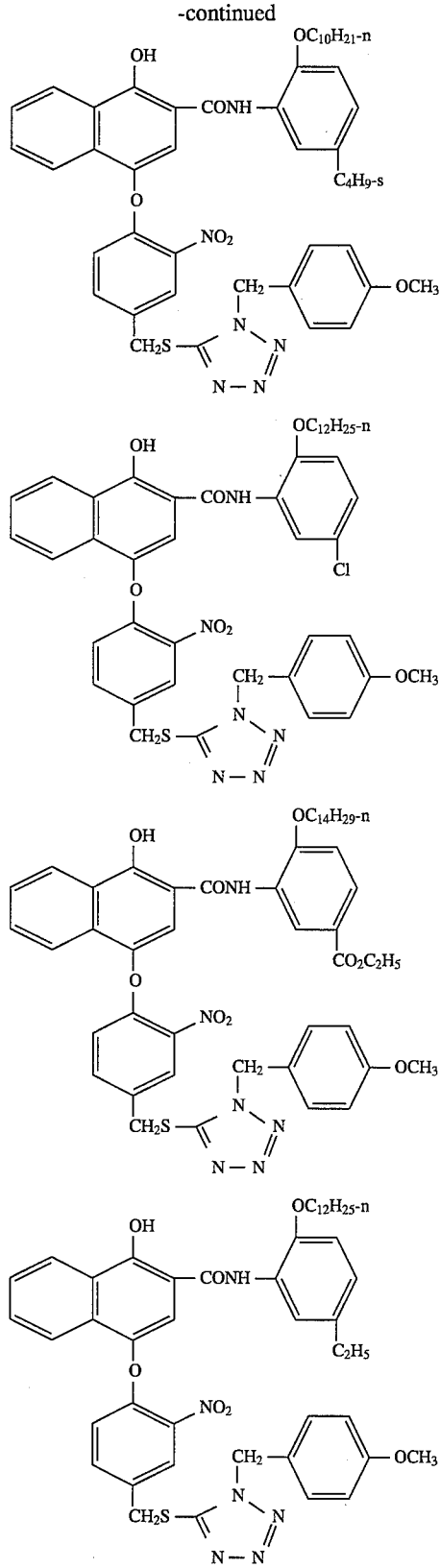

37
-continued
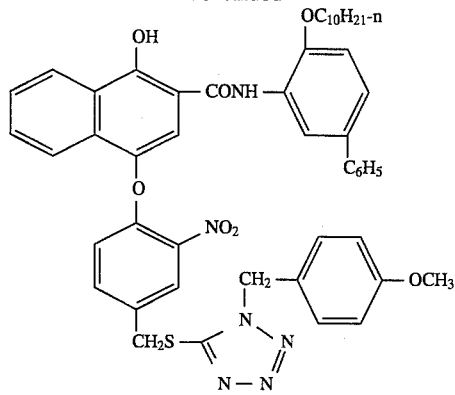
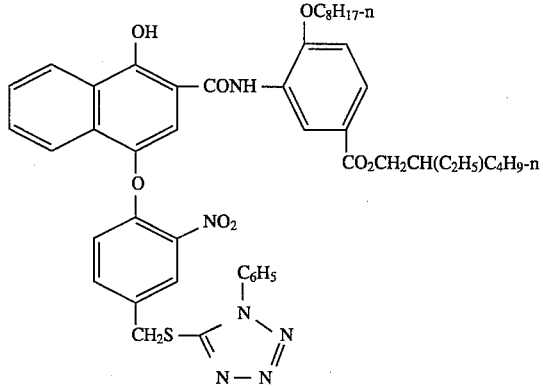
38
-continued
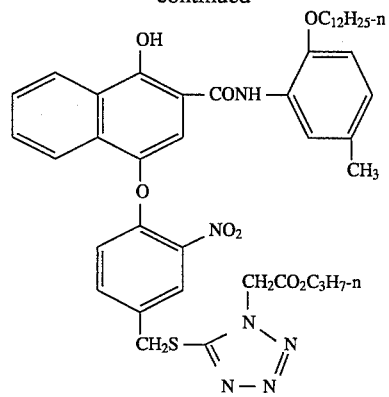
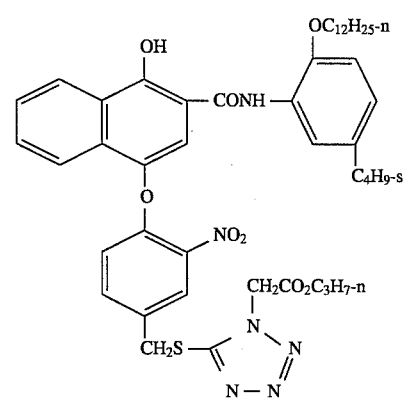
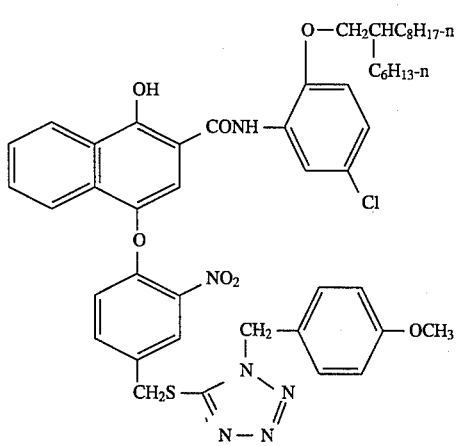
and
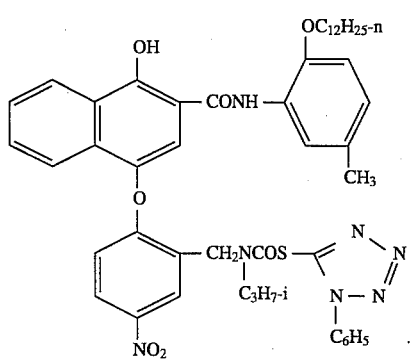
12. A photographic element according to claim 11 wherein the image-modifying coupler is selected from the group consisting of

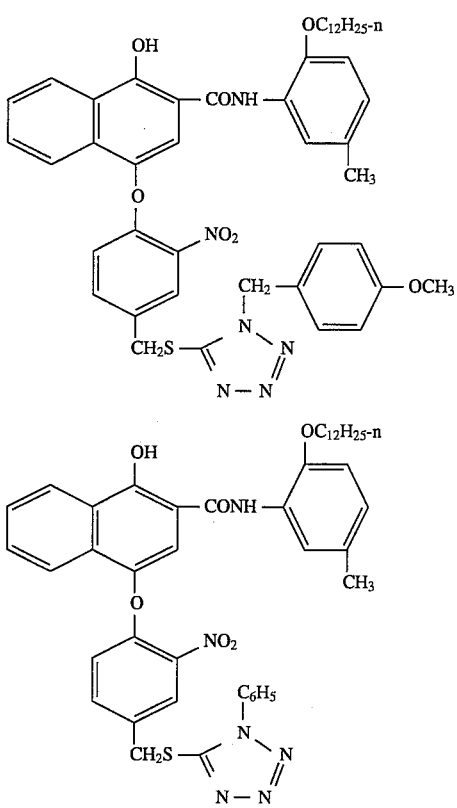

and

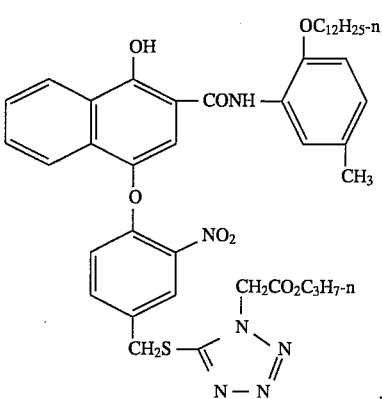

13. A photographic element according to claim 2 further comprising a cyan dye-forming 2-phenylureido-5-carbonamidophenol imaging coupler.

14. A photographic element according to claim 2 wherein said image-modifying coupler is present in amounts between about 0.002 and about 0.40 grams per square meter silver.

15. A photographic element comprising a support bearing (a) at least one silver halide emulsion and (b) at least one cyan dye-forming 2-phenylcarbamoyl-1-naphthol image-modifying coupler having the structure:

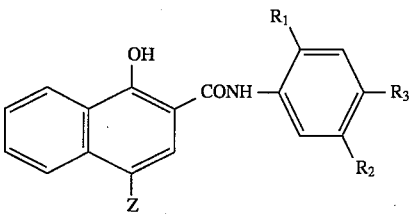

wherein:

$R_1$ is selected from an alkoxy group, a phenoxy group and halogen;

$R_2$ is selected from the group consisting of an alkyl group, a phenyl group, an alkoxy group, and a halogen; with the proviso that when $R_2$ is a halogen, $R_1$ is an alkoxy or phenoxy group;

$R_3$ is selected from hydrogen, and an alkyl group;

$R_1$, $R_2$, and $R_3$ together contain at least 3 carbon atoms; and

Z is a development inhibitor releasing group having the structure

wherein:

IN is a development inhibitor moiety;

TIME is a timing group or switch capable of releasing the development inhibitor moiety by means of intramolecular nucleophilic displacement reaction or electron transfer reaction down a conjugated chain; and w is 1, 2, or 3.

16. A photographic element according to claim 15 wherein when $R_2$ is an alkoxy group, it is unbranched, unsubstituted; and when $R_1$ is an alkoxy group, it is unbranched and unsubstituted.

17. A photographic element according to claim 15 wherein $R_1$ is an unsubstituted, unbranched alkoxy group, $R_2$ is an unsubstituted alkyl group, and $R_3$ is hydrogen.

18. A photographic element according to claim 17 wherein $R_1$ is an n-dodecyloxy group and $R_2$ is a methyl group.

19. A photographic element according to claim 17 wherein $R_1$ is selected from an n-dodecyloxy group and an n-decyloxy group, and $R_2$ is a secondary butyl group.

* * * * *